US007470247B2

(12) United States Patent
Aliski et al.

(10) Patent No.: US 7,470,247 B2
(45) Date of Patent: Dec. 30, 2008

(54) URETERAL STENT

(75) Inventors: Peter Aliski, Newton, MA (US); Vasu Nishtala, Snellville, GA (US); Benedict Shia, Needham, MA (US); Anthony Tremaglio, Charlestown, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 10/832,495

(22) Filed: Apr. 26, 2004

(65) Prior Publication Data

US 2005/0240280 A1  Oct. 27, 2005

(51) Int. Cl.
*A61M 5/00* (2006.01)
*A61F 2/04* (2006.01)
(52) U.S. Cl. ....................... 604/8; 623/23.66
(58) Field of Classification Search ............... None
See application file for complete search history.

(56) References Cited

U.S. PATENT DOCUMENTS

| 3,397,699 | A |   | 8/1968  | Kohl            |         |
|-----------|---|---|---------|-----------------|---------|
| 3,938,529 | A |   | 2/1976  | Gibbons         |         |
| 4,531,933 | A |   | 7/1985  | Norton et al.   |         |
| 4,813,925 | A |   | 3/1989  | Anderson, Jr. et al. |     |
| 4,874,360 | A |   | 10/1989 | Goldberg et al. |         |
| 5,073,166 | A | * | 12/1991 | Parks et al.    | 604/175 |
| 5,167,239 | A |   | 12/1992 | Cohen et al.    |         |
| 5,176,625 | A |   | 1/1993  | Brisson         |         |
| 5,176,626 | A |   | 1/1993  | Soehendra       |         |
| 5,282,860 | A |   | 2/1994  | Matsuno et al.  |         |
| 5,354,263 | A |   | 10/1994 | Coll            |         |
| 5,380,270 | A | * | 1/1995  | Ahmadzadeh      | 604/9   |

(Continued)

FOREIGN PATENT DOCUMENTS

DE        69510973        3/2000

(Continued)

OTHER PUBLICATIONS

Examination Report dated Aug. 4, 2006 from the German Patent Office for corresponding German patent application No. 10-2004-053-543-4-43, filed Nov. 5, 2004, 4 pages.
Examination Report dated Aug. 4, 2006 from the German Patent Office for related German patent application No. 10 2004 050 915.8, filed Oct. 19, 2004, 3 pages.

*Primary Examiner*—Thomas J Sweet
(74) *Attorney, Agent, or Firm*—Ganz Law P.C.

(57) ABSTRACT

A ureteral stent comprising an elongated tubular member having a body portion and opposed distal end portion and proximal end portion, the elongated tubular member defining a lumen therein; a retention disk comprising a plurality of generally axial, spaced-apart collapsable struts interconnected with a membrane to form a generalized tube with a retention disk lumen therein, the retention disk lumen in fluid communication with the lumen of the body portion, the struts and the membrane couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight, as well as a free-resting state wherein each strut folds in upon itself at the folding hinge to form an inverted umbrella-like disk-shaped configuration; and a valve, wherein the inverted umbrella-like configuration provides a conformal shape to the ureteral orifice.

27 Claims, 5 Drawing Sheets

U.S. PATENT DOCUMENTS

| | | | |
|---|---|---|---|
| 5,518,498 A | 5/1996 | Lindenberg et al. | |
| 5,599,291 A | 2/1997 | Balbierz et al. | |
| 5,681,274 A | 10/1997 | Perkins et al. | |
| 5,766,209 A * | 6/1998 | Devonec | 604/8 |
| 5,964,744 A | 10/1999 | Balbierz et al. | |
| 6,214,036 B1 | 4/2001 | Letendre et al. | |
| 6,258,117 B1 | 7/2001 | Camrud et al. | |
| 6,267,783 B1 | 7/2001 | Letendre et al. | |
| 6,350,252 B2 * | 2/2002 | Ray et al. | 604/107 |
| 6,368,356 B1 | 4/2002 | Zhong et al. | |
| 6,395,021 B1 | 5/2002 | Hart et al. | |
| 6,582,472 B2 | 6/2003 | Hart | |
| 6,685,744 B2 | 2/2004 | Gellman et al. | |
| 6,709,465 B2 | 3/2004 | Mitchell et al. | |
| 6,764,519 B2 | 7/2004 | Whitmore, III | |
| 6,887,215 B2 | 5/2005 | McWeeney | |
| 6,908,447 B2 * | 6/2005 | McWeeney et al. | 604/9 |
| 6,913,625 B2 * | 7/2005 | Segura et al. | 623/23.7 |
| 6,921,378 B2 | 7/2005 | O'Keele et al. | |
| 6,929,663 B2 * | 8/2005 | Rioux et al. | 623/23.64 |
| 6,949,125 B2 | 9/2005 | Robertson | |
| 7,041,139 B2 | 5/2006 | Bluni et al. | |
| 2001/0053936 A1 | 12/2001 | Withmore, III | |
| 2002/0183852 A1 | 12/2002 | McWeeney | |
| 2003/0018291 A1 * | 1/2003 | Hill et al. | 604/8 |
| 2003/0040803 A1 | 2/2003 | Rioux et al. | |
| 2003/0163204 A1 * | 8/2003 | Rix | 623/23.7 |
| 2003/0176831 A1 | 9/2003 | Gellman et al. | |
| 2004/0087886 A1 * | 5/2004 | Gellman | 604/8 |
| 2005/0165366 A1 | 7/2005 | Brustad et al. | |
| 2005/0187510 A1 | 8/2005 | McWeeney | |
| 2005/0240141 A1 | 10/2005 | Aliski et al. | |
| 2005/0240277 A1 | 10/2005 | Aliski et al. | |
| 2005/0240278 A1 | 10/2005 | Aliski et al. | |
| 2005/0246038 A1 | 11/2005 | O'Keele et al. | |
| 2006/0015190 A1 | 1/2006 | Robertson | |

FOREIGN PATENT DOCUMENTS

| | | |
|---|---|---|
| DE | 10155767 | 5/2003 |
| EP | 00365269 | 4/1990 |
| EP | 00516189 | 12/1992 |
| EP | 0593948 | 4/1994 |
| EP | 1214917 | 6/2002 |
| WO | WO96/11721 | 4/1996 |
| WO | WO00/62708 | 10/2000 |
| WO | WO/02/098500 | 12/2002 |
| WO | WO03/030981 | 4/2003 |
| WO | WO03/075795 | 9/2003 |
| WO | WO03/079930 | 10/2003 |
| WO | WO03/079934 | 10/2003 |
| WO | WO03/089038 | 10/2003 |

* cited by examiner

URETERAL STENT

FIELD OF THE INVENTION

The present invention is related to ureteral stents, and more particularly, to methods and apparatus for preventing stent migration and reflux flow.

BACKGROUND

Tubular prostheses, commonly referred to as stents, are used in a variety of medical procedures. For example, stents are often used in connection with assisting drainage from the kidney through the ureter, from the liver through the biliary ducts, from the dorsal or ventral pancreas through the pancreatic ducts, from the gall bladder through the cystic, hepatic, or common bile ducts, and the like. A leading reason for stent deployment in ducts is to provide drainage to circumvent a blockage. Blockage of ducts in the body can be a serious and very painful affliction that can result in death if not promptly and effectively treated. Blockages can occur for a number of reasons. For example, stones or debris from such stones can pass from the kidney into the ureter, where they become entrapped. Similarly, stones or debris can pass from the gall bladder into the bile ducts, where they become entrapped. Alternatively, cysts or tumors growing against the outer wall of the ducts can cause constriction of the ducts. Similarly, internal or duct wall cysts or tumors can act to block ducts.

The main function of ureteral stents, for example, is to bypass ureteral obstruction and to provide urinary drainage from the kidney to the bladder for a period of time, typically a few days to several months. The ureteral stent is usually provided with drainage means such as a lumen for directing fluid from the renal pelvis to the bladder. Conventional stents include openings provided along the stent for communication with the lumen to aide in drainage.

Early ureteral stents were straight. As a result, after placement into the ureter, these straight stents often migrated or were expelled from the ureter as a result of peristaltic action by the ureter. Later ureteral stents, therefore, were usually designed with means of retention on one or both ends of the stent. The retention means is intended to inhibit stent migration either upward into the kidney or downward into the bladder. Retention means that have been employed are in the form of hooks, pigtails, coils, corkscrews, malecots, barbs, mushrooms, or any other practical shape that will serve the purpose.

In addition to varying lengths, ureteral stents are also made with varying diameters, e.g., from 3 French (1 mm) to 16 French (5.28 mm), and typically, 4.5 French (1.5 mm) to 8.5 French (2.8 mm), and varying degrees of hardness. Ureteral stents with smaller diameters are usually easier to insert but may provide insufficient drainage, whereas stents with larger diameters allow for increasing drainage capacity through the ureter but may be difficult to insert.

Current urinary stents comprise a shaft commonly made of either single or dual durometer polymer material. Current shaft designs often have unique profile cross-sections and hydrophilic or anti-microbial coatings, for example. This shaft typically resides in the ureter to provide drainage of urine after ureteroscopy procedures. Stiff ureteral stents are easier to insert than are softer stents, but once inserted can lead to increased patient discomfort. Stiff stents are less likely to accommodate the dynamic urinary tract anatomy that stretches and relaxes. The relative push and pull of the kidney and bladder is not accommodated for, therefore increasing patient discomfort from contact irritation of the stent within the anatomy. In addition, the lack of accommodation of the normal body movements increases the potential for the stent to migrate or dislodge from its intended location.

Anecdotally, it is believed that the softer the material, the less irritation to the ureter, and the greater the patient comfort. The lack of stiffness makes it difficult to push the stent in place, however. Hence for placement, a certain axial stiffness is built in which equates to a high level of radial stiffness. Stiff stents are believed to be felt by the muscle spasm of the ureter potentially causing patient discomfort. Further, the axial stiffness of current stents may not be ideal for comfort to the urinary tract anatomy without being felt by the patient.

Presently, most available stents are either made of silicone or of a harder polymer. Silicone may increase patient comfort, but because of the softness of silicone, it is more difficult to guide the stent into the ureter. Once in the ureter, the softness of the silicone increases the likelihood of migration of the stent because rigid retention means are not available.

Thus, although stents have been designed to address one or more of the above problems specifically, there are currently no devices incorporating features that can be used to bypass most of the aforementioned disadvantages. It would thus be desirable to have a stent that provides one or more of the following attributes, easy insertion or implantation, strong retention, and increase patient comfort.

Urinary stent typically have a bladder curl made from a soft material to prevent migration and irritation. Patient discomfort from these stents come from a number of areas. One such area is that the bladder curl can rub and irritate the inside of the bladder, especially the sensitive trigone area. Another such area is that flank pain is perceived by the patient due to the reflux occurring as the bladder voids and urine is pushed up through the stent lumen back into the kidney.

BRIEF DESCRIPTION OF THE DRAWINGS

Like reference numbers indicate corresponding elements in the figures.

SUMMARY OF THE INVENTION

The present invention provides embodiments of medical devices that provide for fluid drainage while both maintaining patient comfort.

An embodiment of the present invention relates to a ureteral stent comprising an elongated tubular member having a body portion and opposed distal end portion and proximal end portion, the elongated tubular member defining a lumen therein; a retention disk comprising a plurality of generally axial, spaced-apart collapsable struts interconnected with a membrane to form a generalized tube with a retention disk lumen therein, the retention disk lumen in fluid communication with the lumen of the body portion, the struts and the membrane couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight, as well as a free-resting state wherein each strut folds in upon itself at the folding hinge to form an inverted umbrella-like disk-shaped configuration; and a valve, wherein the inverted umbrella-like configuration provides a conformal shape to the ureteral orifice.

DETAILED DESCRIPTION

Reference will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

The invention relates to embodiments of medical devices (e.g., stents) for draining fluids. The invention increases patient comfort and prevents fluid retention if a stricture in a vessel develops. For simplicity and illustrative purposes, embodiments of the invention are described herein the context of draining urine from a kidney, through a ureter, and into the bladder. However, the invention is applicable to any situation that requires drainage within a body, from a body, and from one body structure to another. One such situation is, for example, biliary drainage from the gall bladder, through the biliary ducts, to the duodenum.

Figure 1:
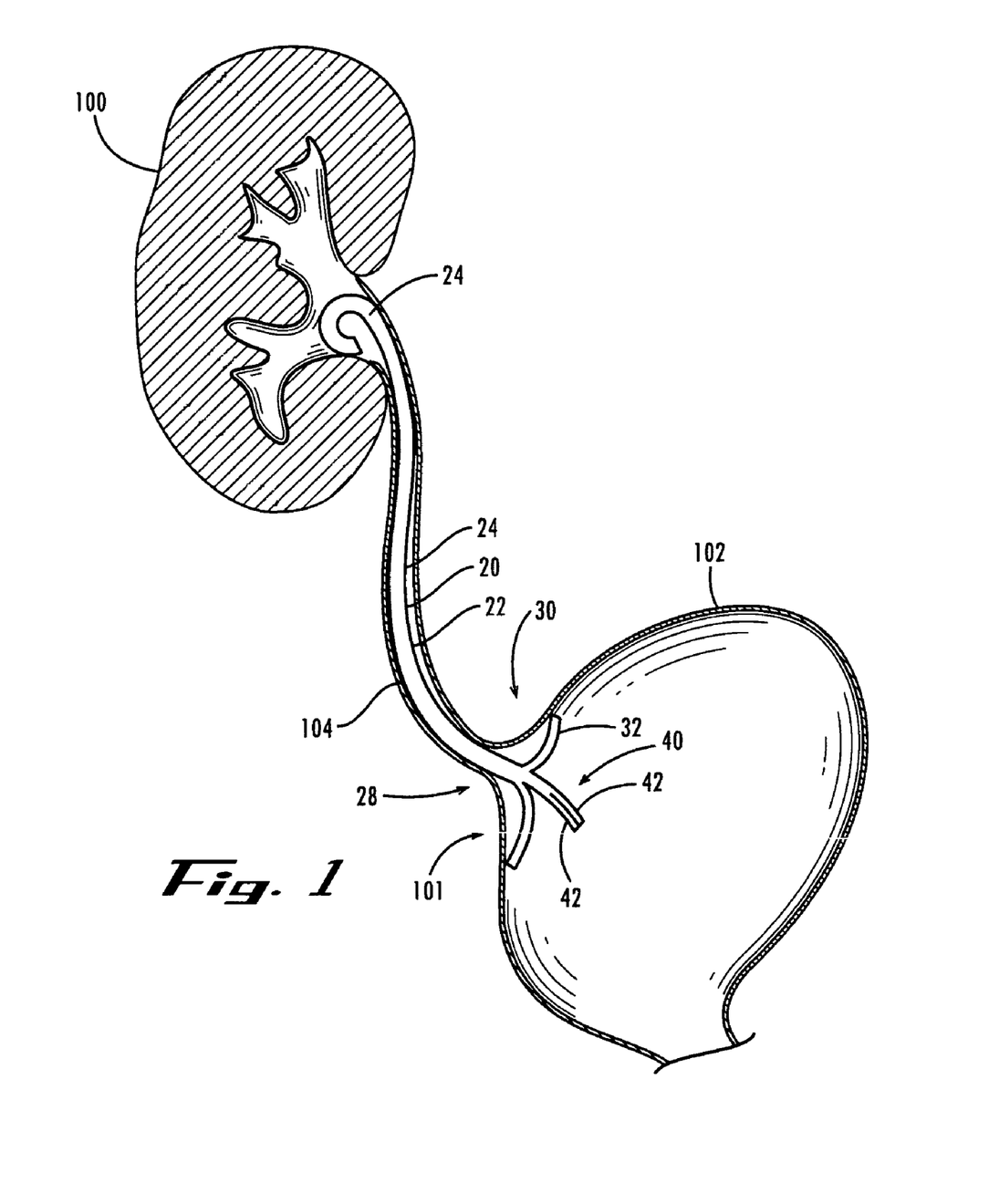
FIG. 1 is a front partial cross-sectional view of a ureteral stent within anatomy in accordance with an embodiment of the present invention.

FIG. 1 is a front partial cross-sectional view of a ureteral stent 10 within anatomy in accordance with an embodiment of the present invention. The stent 10 comprises an elongated tubular member 20 having a relatively straight body portion 22 and opposed distal end portion 24 and proximal end portion 28, a retention disk 30, and a valve 40. The distal end portion 24 is provided with means for retaining the distal end portion 24 in a kidney 100, such as the conventional loop as shown. The body portion 22 is adapted to be inserted into and reside substantially in the ureter 104.

Figure 2A:
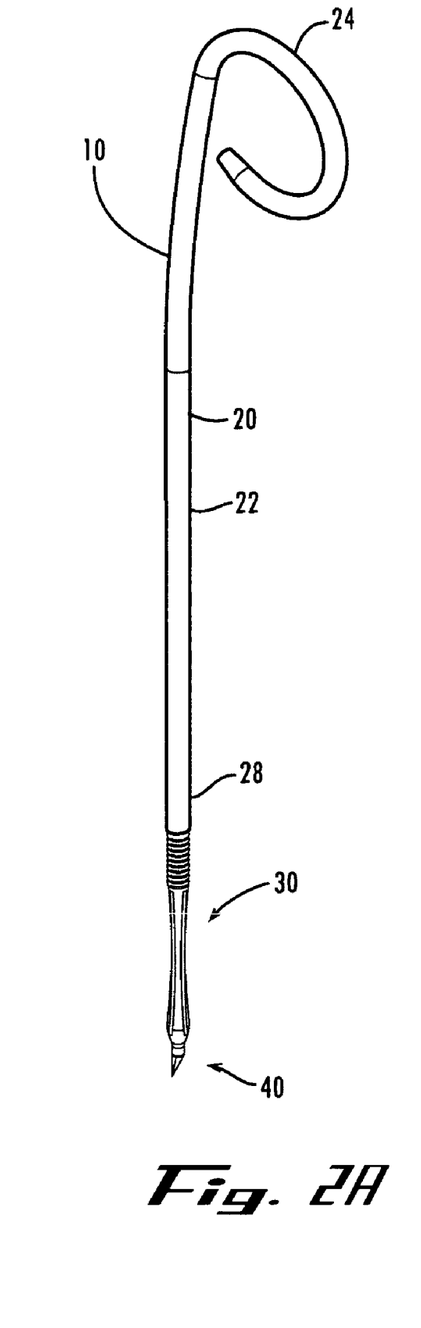
FIG. 2A is a perspective view of a stent in accordance with the embodiment of FIG. 1.
Figure 2B:
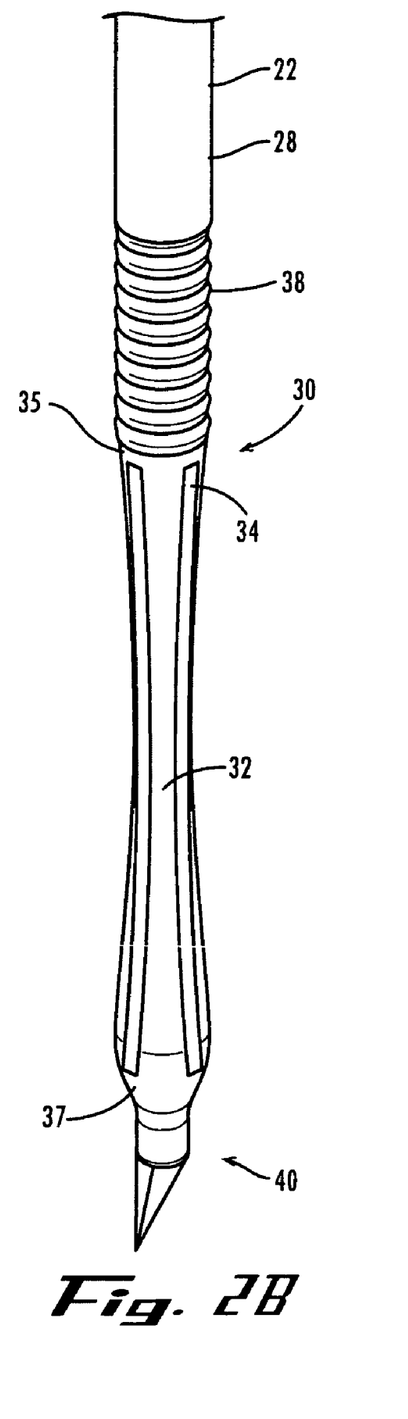
FIG. 2B is a perspective view of the stent proximal end portion comprising a retention disk and a valve in a pre-deployed configuration, in accordance with an embodiment of the present invention.
Figures 3, 4:
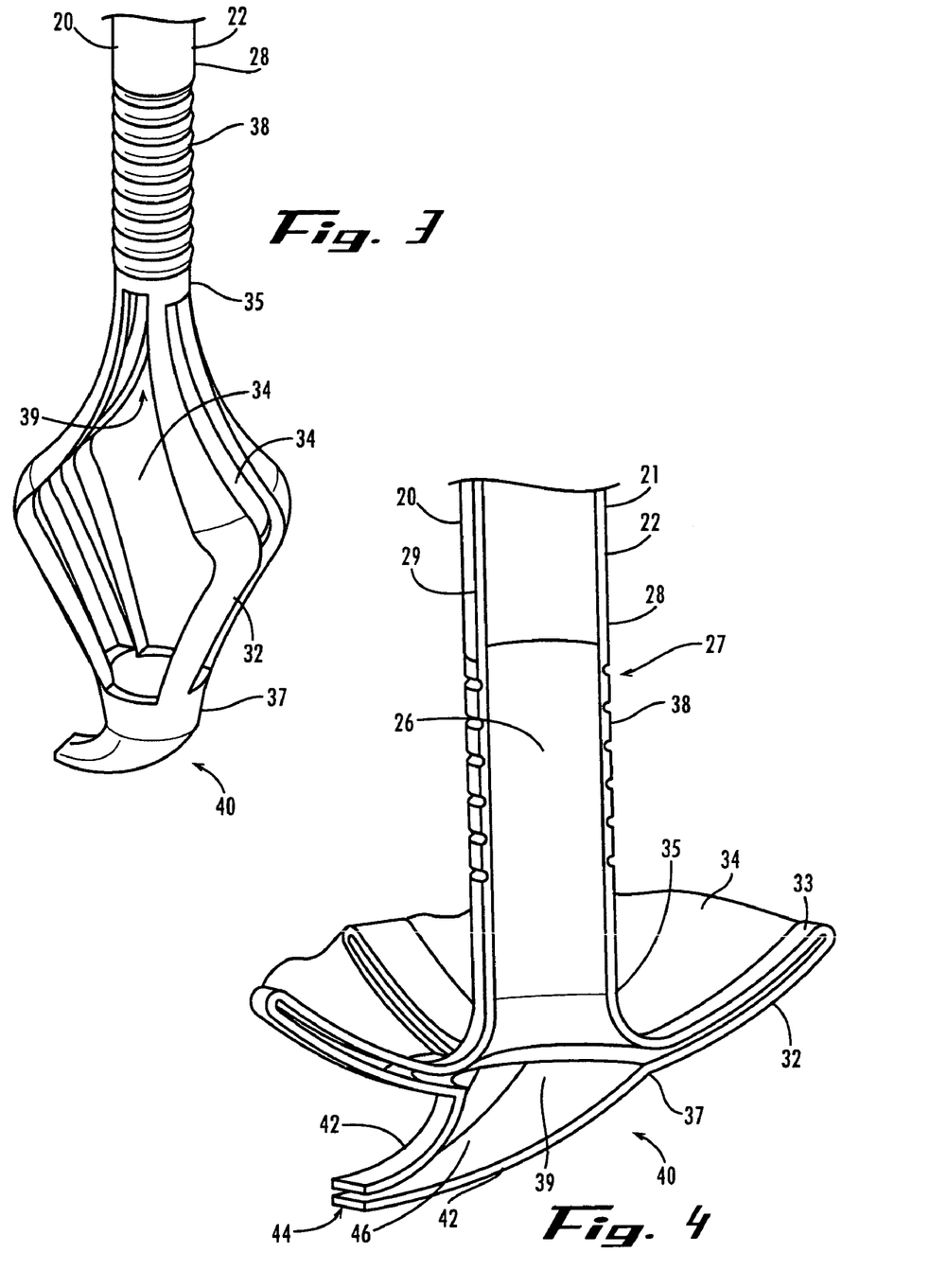
FIG. 3 is a perspective view of the stent proximal end portion comprising a retention disk and a valve undergoing deployment, in accordance with an embodiment of the present invention.
FIG. 4 is a perspective view of the stent proximal end portion comprising a retention disk and a valve in a deployed configuration, in accordance with an embodiment of the present invention.
Figure 5:
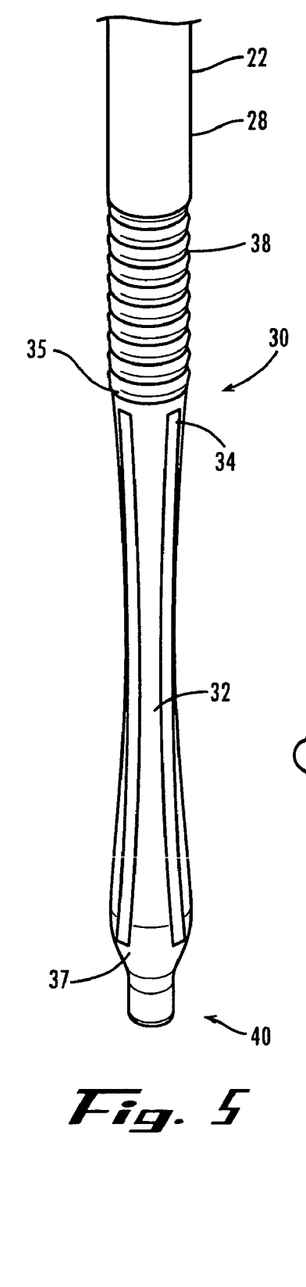
FIG. 5 is a perspective view of a stent proximal end portion comprising a retention disk in a pre-deployed configuration, in accordance with an embodiment of the present invention.
Figure 6:
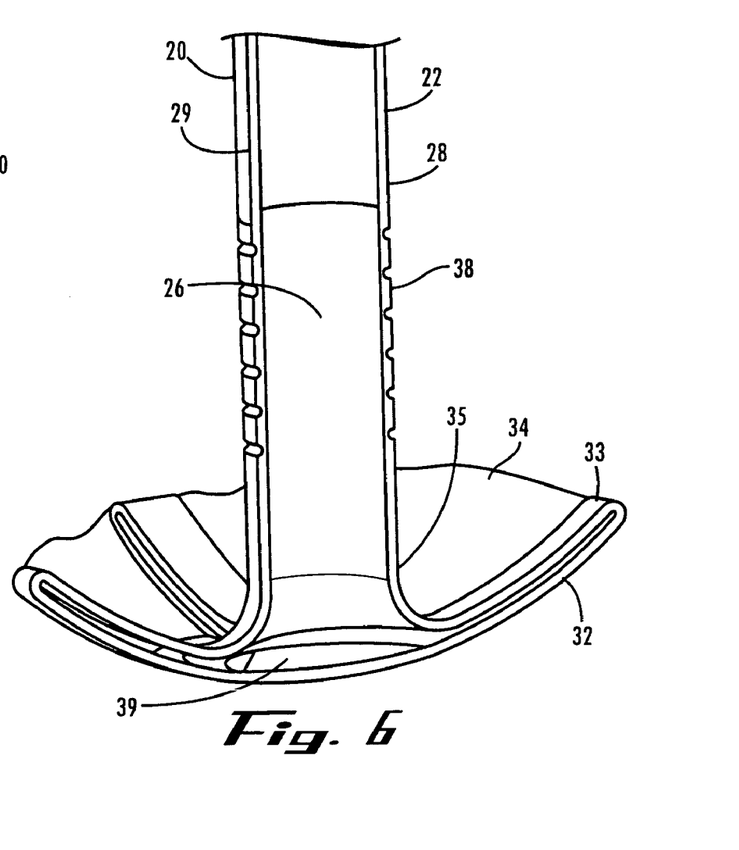
FIG. 6 is a perspective view of the stent proximal end portion comprising a retention disk in a deployed configuration, in accordance with an embodiment of the present invention.
Figure 7:
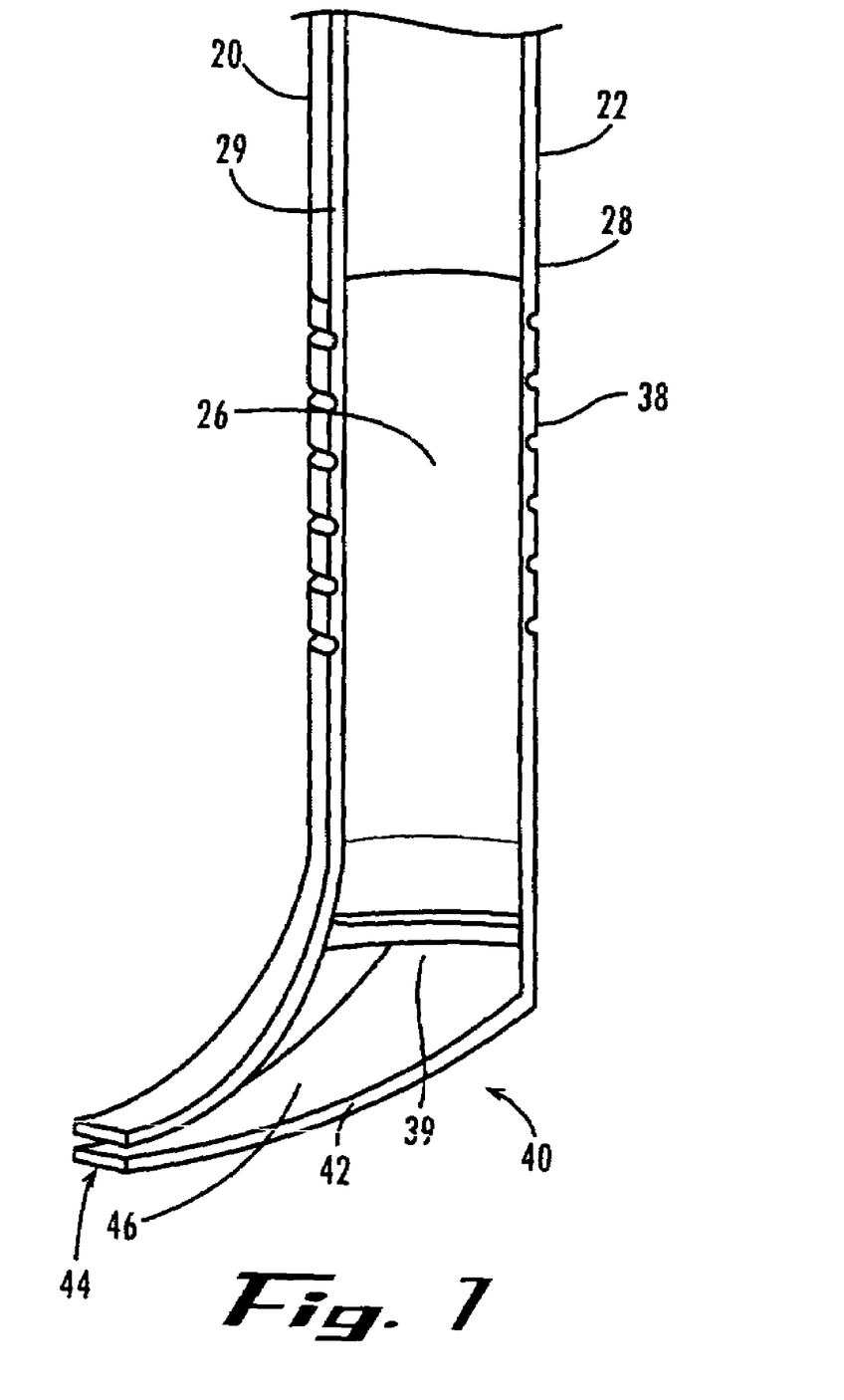
FIG. 7 is a perspective view of the stent proximal end portion comprising a valve, in accordance with an embodiment of the present invention.

FIGS. 2A, 2B, 3, and 4 are perspective, partial perspective, partial perspective, and cross-sectional views, respectively, of the proximal end portion 28, retention disk 30, and valve 40, at three-stages of deployment, in accordance with an embodiment of the present invention. FIGS. 2A and 2B illustrate a pre-deployment configuration, wherein the retention disk 30 is retained in an extended orientation. FIG. 3 illustrates a partially deployed configuration, wherein the retention disk is expanding radially and contracting axially. FIG. 4 illustrates the fully deployed, free state configuration of the retention disk 30 forming an umbrella-like configuration.

The body portion 22 comprises an elongated tubular member 20 having a wall 29 defining a lumen 26 therein. The tubular member 20 may be formed from a variety of known materials which are biocompatible and have desired physical properties to be fabricated in the form hereafter described. Examples of suitable materials include, but not limited to, silicone, thermoplastic materials, elastomers, or any material known to one skilled in the art.

The retention disk 30 comprises a plurality of generally, axial, spaced-apart collapsible struts 32 interconnected at their edges with a plurality of thin-wall resilient non-permeable membranes 34 coupled to and spanning the area in between the struts, but not covering the struts, to form a generalized tube with a retention disk lumen 39 therein. The retention disk lumen 39 is in fluid communication with the lumen 26 of the body portion 22. The struts 32 and the membrane 34 couple to the body portion proximal end 28 at a retention disk distal end 35 and terminate at a retention disk proximal end 37.

Each strut 32 is an elongated member having a widthwise folding hinge 33 substantially dividing the length of the strut 32 in half. The struts 32 are adapted to have an expanded state wherein the struts 32 are unfolded and substantially straight, as well as a free-resting state wherein each strut 32 folds in upon itself at the folding hinge 33 to form an inverted umbrella-like disk-shaped configuration. The inverted umbrella-like configuration provides a conformal shape to the ureteral orifice 101 as shown in FIG. 1. Further, the umbrella-like configuration substantially prevents the stent 10 from irritating the trigone area of the bladder 102. Further, the umbrella-like configuration provides a seal between the ureteral orifice 101 and the retention disk 30, the importance of which will be discussed below with respect to the valve 40.

The struts 32 comprise a material suitable for the particular purpose, such as, but not limited to, stainless steel and nickel-titanium alloy. Certain alloys of nickel-titanium are known as Nitinol and can be provided with a super-elastic shape-memory physical property. A super-elastic property provides a high degree of flexibility without elastic deformation which is a desired property for the particular purpose. The shape-memory property provides a predetermined restoring configuration also suitable for the particular purpose.

The membrane 34 comprises a relatively low durometer material. Suitable material for the membrane 34 includes, but not limited to, silicone, although other soft polymer materials could be used. The membrane 34 comprise a material that is elastic and allows for the radially expansion of the struts 32.

In other embodiments in accordance with the present invention, the membrane 34 comprises a non-elastic material that folds down in the pre-deployed configuration. Upon deployment of the retention disk 30, the retention disk lumen 39 shortens to substantially form an orifice in communication with the lumen 26 of the body portion 22.

The valve 40 is coupled to the retention disk proximal end 37. The valve 40 comprises at least two valve lips 42 that couple to the retention disk proximal end 37 and converge in engagement at a valve opening 44. The valve lips 42 define a lumen 46 therebetween and in communication with the retention disk lumen 39, and thus, with the lumen 26 of the body portion 22 and therefore with the kidney 100.

The valve lips 42 press together at the valve opening 44 creating a tight seal against the passage of fluids up to a certain head pressure. The valve lips 42 are held elastically in a closed position by means of a force inherent in the shape and material of valve lips 42 and/or imparted by an elastic element (for example a thin elastic band, not shown) which exerts its force, preferably adjustable, to urge the valve lips 42 closed.

When the force due to the pressure of the fluid coming from the lumen 26 on the valve lips 42 exceeds the force due to the elasticity of the materials, the valve 40 opens and the fluid exits the valve 40 and enters the bladder 102. The valve 40 closes when pressure in the bladder is increased, such as during voiding. When the bladder 102 is being voided, the valve 40 is functionally sealed by the valve lips 42. This serves to stop fluid pressure waves, pulsed or otherwise, from the bladder 104 towards the kidney 100.

In accordance with another embodiment of the present invention, the valve opening 44 remains slightly open in the relaxed state to permit fluid flow and closes tightly upon increased pressure in the bladder, such as during voiding.

In an embodiment in accordance with the present invention, at least a portion of length of the proximal end portion 28 comprises a flexible portion 38. The flexible portion 38 is characterized by exhibiting a physical property that provides both longitudinal elasticity allowing for stretch and recoil, as well as radial elasticity allowing for bending and recovery.

In an embodiment in accordance with the present invention, the flexible portion 38 is characterized as a region having material of differing material properties than the body portion 22. The body portion 22 comprises a material having a less compliant material property (harder) transitioning to a more compliant (softer) material. In production, this can be accomplished by, for example, a co-extrusion process where deposition of a first material is gradually ceased and deposition of a second is gradually increased.

In another embodiment in accordance with the present invention, the flexible portion 38 is characterized as a region of thinning of the wall 21 of the tubular member 20, wherein the tubular member 20 comprises a homogenous material. The body portion 22 comprises a wall 21 of a predetermined thickness and the flexible portion 38 comprises a wall of a smaller predetermined thickness. In production, this can be accomplished by, for example, a co-extrusion process where deposition of a material is gradually reduced over the length of the flexible portion 38.

In another embodiment in accordance with the present invention, the flexible portion 38 is characterized as a region of geometric change, such as, but not limited to corrugations 27, of the wall 21 of the tubular member 20, wherein the tubular member 20 comprises a homogenous material. The body portion 22 comprises a wall 21 of a predetermined thickness and the flexible portion 38 comprises a wall having ripples or corrugations 27 so as to impart a more flexible property.

It is appreciated that a stent 10, in accordance with the present invention, may comprise a valve 40, a retention disk 30, a flexible portion 38, or combinations thereof. In another embodiment in accordance with the present invention, the stent 110 comprises a body portion 22 and a valve 40. In this embodiment, the stent 110 is provided with the benefits of the valve 40.

Referring again to FIG. 1, the stent 10 includes a body portion 22 adapted to be positioned within the ureter 104. The stent 10 thereby provides fluid communication along its length from the distal end portion 24 to the proximal end portion 28, and to the valve 40; fluid communication between the kidney 100 and bladder 102 is maintained through the stent 10.

Once a physician has selected a stent 10 for use in the patient, after considering the normal size of the ureteral passage and the length of the ureter 104, the placement of the ureteral stent 10 may by accomplished in accordance with known prior art techniques. A wire stylet, or guidewire, (not shown) which can be formed of stainless steel, is inserted into the valve opening 44 and retention disk 30, the proximal end portion 28 of the stent 10 and into the lumen 26 and advanced into the distal end portion 24.

Confirmation that the renal pelvis has been entered by the distal end portion 24 can be obtained by x-ray. If desired, radiopaque measurement markings or other suitable radiopaque indicia can be incorporated on the stent 10 and are visible during x-ray examination to aid in confirming the position of the stent 10.

After the distal end portion 24 has been inserted into a predetermined distance into the renal pelvis, the guidewire is withdrawn, enabling the retention disk 30 to deploy. The retention disk 30 bears against the walls of the renal cavity 101 at the ureter orifice 104.

Alternatively, the ureteral stent 10 may be placed in the anatomy during surgery.

Dimensions for the ureteral stent 10 of the present invention are not critical, however, they include internal diameters of 4.5 to 8.5 French, and lengths ranging from 20 cm. to 32 cm.

In certain embodiments of medical devices according to the invention, the body portion 22 may have, for example, a circular cross-section. The circular cross-section may be of any circumference that is of suitable size for the body structure into which the device is placed. For example, for use in the kidney 100, ureter 104, and bladder 102, the body portion 22 may be from about 8.0 French to about 4.8 French in size. The stent 10 may have a substantially constant cross-sectional area along its length. Alternatively, the stent 10 may be tapered from about the distal end portion 24 to about the proximal end portion 28 with the size of the section decreasing from about 7 French to about 3 French. Other French sizes and tapering configurations are useful depending upon either the average size in a population or the actual size in an individual of the body structure or structures into which the device is placed.

The tubular member 20 according to the invention may be constructed from any of a number of materials. Those materials that are useful include, for example, materials that are able to flex but also retain their shape, to a degree, when they are perturbed. Additionally, useful materials are, for example, materials that have a resilient quality, being able to regain at least some of their original shape when the stent 10 ceases to be perturbed and/or resist, for example, compression. One such material that combines these features is Percuflex™. Moreover, thermo-formable materials, including, for example, Percuflex™ are useful in the practice of the invention.

Identical concerns that are mentioned above with respect to stents are also applicable in the catheter and intubation arts, which include, without limitation: intravenous catheters, guiding catheters, sheaths, umbilical catheters, trocar catheters, heart catheters (including, valvostomy catheters, angioplasty catheters, arthroscopy catheters, and the like), perfusion catheters, suction catheters, oxygen catheters, endoscopy catheters, endotracheal tubes, stomach tubes, feeding tubes, lavage tubes, rectal tubes, urological tubes, irrigation tubes, aneurysm shunts, stenosis dialators, trocars, and inserters, generally.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A stent comprising:
an elongated tubular member having a body portion, a proximate end portion and a distal end portion, the tubular member having an axial lumen therein adapted to provide fluid communication from the distal end portion to the proximal end portion; and
a retention disk comprising a first, pre-deployment configuration wherein a plurality of generally axial, spaced-apart collapsable struts interconnected with a membrane form a generalized tube with a retention disk lumen therein, the retention disk lumen in fluid communication with the lumen of the body portion, the struts and the membrane couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight; and a second, fully deployed, free state configuration wherein each strut folds in upon itself in a free resting state at the folding hinge to form an inverted umbrella-like disk-shaped configuration, and wherein the retention disk is biased to a fully deployed umbrella-like shaped configuration.

2. The stent of claim 1, wherein the inverted umbrella-like configuration is adapted to provide a conformal shape to the ureteral orifice.

3. The stent of claim 1, wherein the umbrella-like configuration substantially prevents the stent from irritating the trigone area of the bladder.

4. The stent of claim 1, wherein the umbrella-like configuration provides a seal between the ureteral orifice and the retention disk.

5. The stent of claim 1, wherein the struts comprise nickel-titanium alloy.

6. The stent of claim 1, wherein the membrane comprises a relatively low durometer material.

7. The stent of claim 1, wherein the membrane comprise a material that is elastic and allows for the radially expansion of the struts.

8. The stent of claim 1, further comprising a valve coupled to the retention disk proximal end, the valve comprising at least two valve lips that couple the retention disk proximal end and converge in engagement at a valve opening, the valve lips defining a lumen therebetween and in communication with the retention disk lumen.

9. The stent of claim 8, wherein the valve lips press together at the valve opening creating a tight seal against the passage of fluids up to a certain head pressure.

10. The stent of claim 8, wherein the valve lips are held elastically in a closed position by means of a force inherent in the shape and material of valve lips.

11. The stent of claim 8, wherein the valve lips open under the force due to the pressure of the fluid coming from the lumen, the force exceeding the force due to the elasticity of the materials.

12. The stent of claim 8, wherein the valve is functionally sealed by the valve lips when pressure in the bladder is increased, such as during voiding.

13. The stent of claim 8, wherein the valve opening remains slightly open in the relaxed state to permit fluid flow and closes tightly upon increased pressure in the bladder, such as during voiding.

14. The stent of claim 1, further comprising:
at least a portion of the proximal end portion comprises a flexible portion adapted to provide both longitudinal elasticity allowing for stretch and recoil, as well as radial elasticity allowing for bending and recovery.

15. The stent of claim 14, wherein the flexible portion is a region having material of differing material properties than the body portion.

16. The stent of claim 14, wherein the flexible portion is characterized as a region of thinning of a wall of the tubular member.

17. The stent of claim 14, wherein the flexible portion comprises a geometric change adapted to impart a more flexible property.

18. The stent of claim 14, further comprising:
a valve coupled to the retention disk proximal end, the valve comprising at least two valve lips that couple the retention disk proximal end and converge in engagement at a valve opening, the valve lips defining a lumen therebetween and in communication with the retention disk lumen; and
wherein the body portion is adapted to be positioned within the ureter, the stent thereby provides fluid communication along its length from the distal end portion to the proximal end portion, to the valve, and to the bladder.

19. A ureteral stent for maintaining drainage between the kidney and bladder comprising:
an elongated tubular member having a body portion, a proximate end portion and a distal end portion, the tubular member having an axial lumen therein adapted to provide fluid communication from the distal end portion to the proximal end portion; and
a retention disk comprising a first, pre-deployment configuration wherein a plurality of generally axial, spaced-apart collapsable struts interconnected with a membrane form a generalized tube with a retention disk lumen therein, the retention disk lumen in fluid communication with the lumen of the body portion, the struts and the membrane couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight; and a second, fully deployed, free state configuration wherein each strut folds in upon itself in a free resting state at the folding hinge to form an inverted umbrella-like disk-shaped configuration, and wherein the retention disk is biased to a fully deployed umbrella-like shaped configuration.

20. The stent of claim 19, further comprising a valve coupled to the retention disk proximal end, the valve comprising at least two valve lips that couple to the retention disk proximal end and converge in engagement at a valve opening, the valve lips defining a lumen therebetween and in communication with the retention disk lumen.

21. The stent of claim 19, further comprising:
at least a portion of the proximal end portion comprises a flexible portion adapted to provide both longitudinal elasticity allowing for stretch and recoil, as well as radial elasticity allowing for bending and recovery.

22. A ureteral stent for maintaining drainage between the kidney and bladder comprising:

an elongated tubular member having a body portion, a proximate end portion and a distal end portion, the tubular member having an axial lumen therein adapted to provide fluid communication from the distal end portion to the proximal end portion; and a retention disk comprising a first, pre-deployment configuration wherein a plurality of generally axial, spaced-apart collapsable struts interconnected with a membrane form a generalized tube with a retention disk lumen therein, the retention disk lumen in fluid communication with the lumen of the body portion, the struts and the membrane couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight; and a second, fully deployed, free state configuration wherein each strut folds in upon itself in a free resting state at the folding hinge to form an inverted umbrella-like disk-shaped configuration, and wherein the retention disk is biased to a fully deployed umbrella-like shaped configuration; and a valve coupled to the retention disk proximal end, the valve comprising at least two valve lips that couple to the retention disk proximal end and converge in engagement at a valve opening, the valve lips defining a lumen therebetween and in communication with the retention disk lumen.

23. A stent comprising:

an elongated tubular member having a body portion, a proximate end portion and a distal end portion, the tubular member having an axial lumen therein adapted to provide fluid communication from the distal end portion to the proximal end portion; and a retention disk comprising a single integrated structure formed of a plurality of struts and membranes, the membranes coupled along the sides of the struts and spanning the area in between the struts, but not covering the struts, and the retention disk having first, pre-deployment configuration wherein the plurality of generally axial, spaced-apart collapsible struts interconnected with membranes in between the struts to form a generalized tube with a retention disk lumen therein, the retention disk lumen in fluid communication with the lumen of the body portion, the struts and the membranes couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight; and a second, fully deployed, free state configuration wherein each strut folds in upon itself in a free resting state at the folding hinge and the membranes expanding in between the struts to form an inverted umbrella-like disk-shaped configuration, and wherein the retention disk is biased to a fully deployed umbrella-like shaped configuration.

24. The stent of claim 23, further comprising a valve coupled to the retention disk proximal end, the valve comprising at least two valve lips that couple the retention disk proximal end and converge in engagement at a valve opening, the valve lips defining a lumen there between and in communication with the retention disk lumen.

25. The stent of claim 23, further comprising:

at least a portion of the proximal end portion comprises a flexible portion adapted to provide both longitudinal elasticity allowing for stretch and recoil, as well as radial elasticity allowing for bending and recovery.

26. A ureteral stent for maintaining drainage between the kidney and bladder comprising:

an elongated tubular member having a body portion, a proximate end portion and a distal end portion, the tubular member having an axial lumen therein adapted to provide fluid communication from the distal end portion to the proximal end portion;

a retention disk comprising a first, pre-deployment configuration wherein a plurality of generally axial, spaced-apart collapsible struts interconnected with edges that couple to a plurality of membranes, each membrane coupled to two struts along lengths of the edge of the strut and spanning the area in between the struts a to form a generalized tube with a retention disk lumen therein, the retention disk lumen in fluid communication with the lumen of the body portion, the struts and the membranes couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight; and a second, fully deployed, free state configuration wherein each strut folds in upon itself in a free resting state at the folding hinge and the struts and membranes form an inverted umbrella-like disk-shaped configuration, and wherein the retention disk is biased to a fully deployed umbrella-like shaped configuration;

wherein each membrane comprises a material that is elastic and allows for radial expansion of the struts; and wherein the struts and membranes expand simultaneously while the retention disk is undergoing deployment.

27. A stent comprising:

an elongated tubular member having a body portion, a proximate end portion and a distal end portion, the tubular member having an axial lumen therein adapted to provide fluid communication from the distal end portion to the proximal end portion;

a retention disk comprising a first, pre-deployment configuration wherein a plurality of generally axial, spaced-apart collapsible struts with a plurality of distinct membranes affixed at the edges of the struts and spanning an area between the struts to form a generalized tube with a retention disk lumen therein, the retention disk lumen in fluid communication with the lumen of the body portion, the struts and the membranes couple to the body portion proximal end at a retention disk distal end and terminate at a retention disk proximal end, each strut having a widthwise folding hinge substantially dividing the length of the strut, the struts adapted to have an expanded state wherein the struts are unfolded and substantially straight; and a second, fully deployed, free state configuration wherein each strut folds in upon itself in a free resting state at the folding hinge to form an inverted umbrella-like disk-shaped configuration, and wherein the retention disk is biased to a fully deployed umbrella-like shaped configuration.

* * * * *